United States Patent [19]

Gabbay

[11] Patent Number: 4,527,549
[45] Date of Patent: Jul. 9, 1985

[54] METHOD OF AND MEANS FOR INTRAAORTIC ASSIST

[75] Inventor: Shlomo Gabbay, Hartsdale, N.Y.

[73] Assignee: Shelhigh Inc., New York, N.Y.

[21] Appl. No.: 430,039

[22] Filed: Sep. 30, 1982

Related U.S. Application Data

[63] Continuation-in-part of Ser. No. 405,707, Aug. 5, 1982, abandoned.

[51] Int. Cl.$^3$ ............................................. A61M 1/03
[52] U.S. Cl. ................................. 128/1 D; 128/344; 604/101
[58] Field of Search ................. 128/1 D, 344; 604/96, 604/101

[56] References Cited

U.S. PATENT DOCUMENTS

| 3,692,018 | 9/1972 | Goetz et al. | 128/1 D |
| 4,276,874 | 7/1981 | Wolvek et al. | 128/1 D |
| 4,284,073 | 8/1981 | Krause et al. | 128/1 D |
| 4,407,271 | 10/1983 | Schiff | 128/1 D |

FOREIGN PATENT DOCUMENTS 929105 4/1980 U.S.S.R. ............................. 128/1 D

Primary Examiner—Dalton L. Truluck
Attorney, Agent, or Firm—Jordan B. Bierman

[57] ABSTRACT

A method and apparatus are described to provide improved cardiac assist by the use of a new form of intraaortic balloon. A single small balloon may be placed in the ascending aorta close to the aortic valve, such placement being effective to produce a substantially stronger augmentation of heart action than with the use of a longer balloon normally placed, for example, in the descending aorta. Multiple small balloons positioned in the aortic arch, with or without a large balloon in the descending aorta, can be used to provide even stronger coronary flows. The external diameter of the balloons in their inflated condition should in all events never be so great as to block the aorta, even when the latter may become contracted.

13 Claims, 7 Drawing Figures

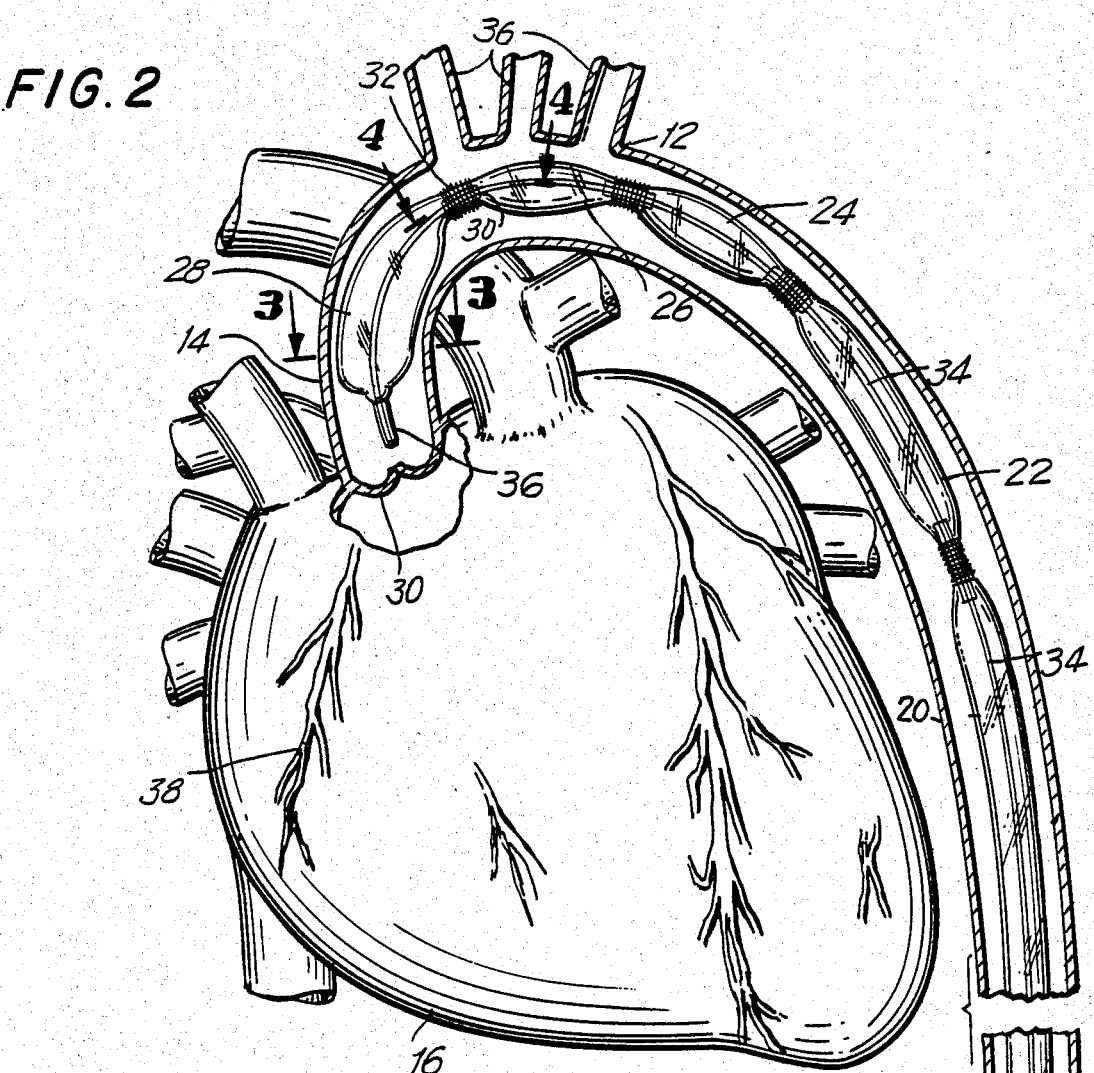
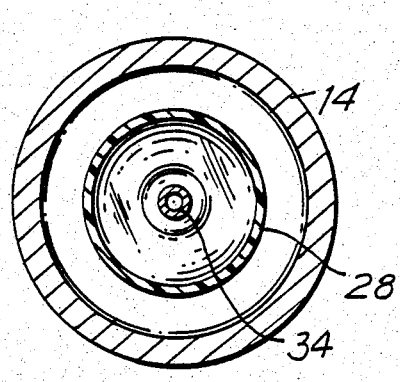
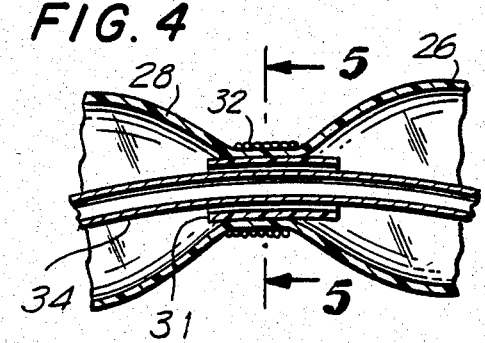
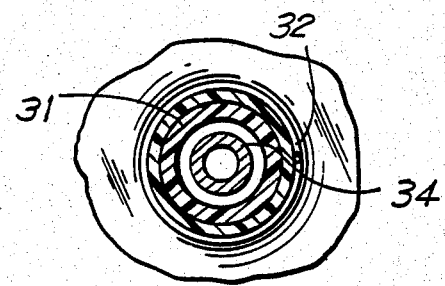

METHOD OF AND MEANS FOR INTRAAORTIC ASSIST

The invention is directed to an improved method and means for intraaortic heart assist, and more particularly to a novel arrangement for substantially increasing the cardiac output in patients suffering from heart failure. This application is a continuation-in-part of my prior application Ser. No. 405,707 filed Aug. 5, 1982, now abandoned.

Counterpulsation by the placement of an inflatable balloon in the descending thoracic aorta to provide diastolic augmentation of blood pressure has become a recognized procedure to augment cardiac output in certain conditions associated with myocardial failure, sometimes called Low Output Syndrome. A single inflatable balloon so positioned is inflated and deflated with a cycle appropriately timed to the normal heart beat. The inflatable balloon pump has become recognized as a useful if imperfect temporary tool whenever circulatory support is required.

However, as discussed in U.S. Pat. No. 3,692,018, Goetz et al., issued Sept. 19, 1972, the simple balloon pump has its limitations. In order to provide a suitable pumping action, it has been made as large as possible with a capacity of about 30 cc, but its very position in the descending aorta results in loss in pressure and pumping action about the heart where, for example, one desires to suffuse the coronary arteries. The shape of the large balloon prevents it from being pushed up about the aortic arch, closer to the heart.

The disadvantages and limitations of the prior art balloon pumps are overcome by the present invention, based upon the discovery supported by actual tests, that it is the position of the balloon pump rather than its size, which plays an important role in its efficacy. More specifically, it has been found in actual tests that a small balloon of 10 cc capacity if placed in the ascending aorta of a dog adjacent the aortic valve can increase cardiac output by 50%. This discovery is particularly fortuitous since it is possible to move a small balloon around the aortic arch with the ascending aorta, and this was of course impossible with the larger size balloon heretofore thought to be necessary.

The invention does not mean that the use of a large balloon in the descending aorta is entirely discarded. As will be described hereinafter, the invention contemplates the use of a single small balloon adjacent the aortic valve either alone, in combination with a large balloon in the descending aorta, or with a series of additional small balloons serially connected between the first small balloon and the large balloon to substantially fill and create pressure and suction within the arch.

The principal object of the invention accordingly is to improve the heart assist procedure by the placement and development of a balloon pump so as to greatly increase cardiac output.

The aforesaid object is attained by positioning a balloon pump in the ascending aorta adjacent the aortic valve. The consequent further object of the invention is to provide a balloon pump structure which can be moved through the aortic arch to the desired position without injuring the internal wall of the arch or the arteries branching therefrom.

These and other objects and advantages of the present invention will become apparent from the following description thereof read in conjunction with the attached drawings in which:

FIG. 2 illustrates the human heart and associated arteries showing in cross-section the positioning of a balloon pump according to this invention, within the descending aorta, the aortic arch and the ascending aorta;

FIG. 3 is a cross-sectional view through the ascending aorta and the implanted balloon pump, taken along the line 3—3 of FIG. 2;

FIG. 4 is a cross-sectional view along the line 4—4 of FIG. 2 illustrating details of interconnected balloons forming the pump;

FIG. 5 is a transverse cross-sectional view along the line 5—5 of FIG. 4;

Figure 1:
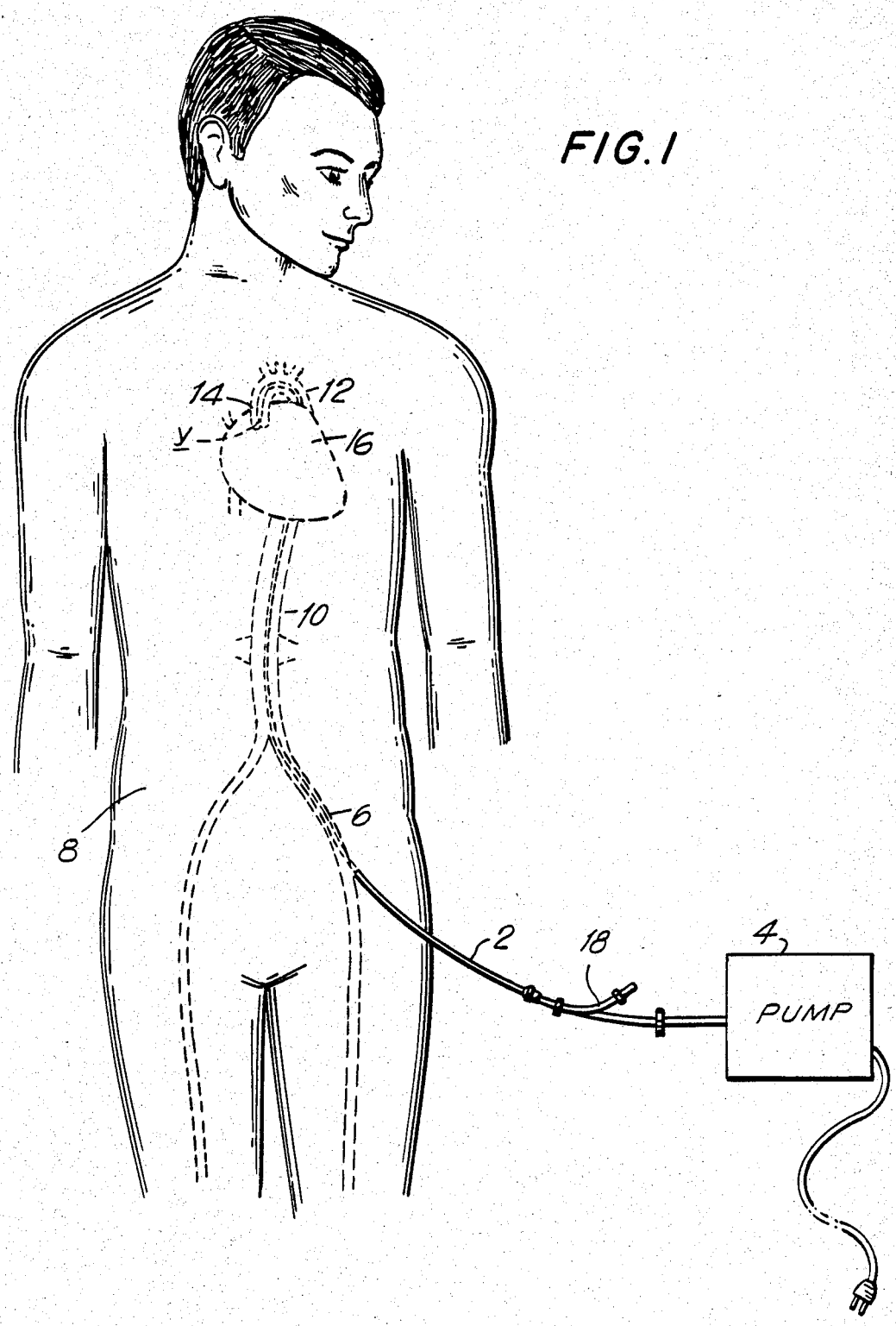
FIG. 1 is a fanciful view of portions of a human body broadly illustrating the invention and positioning of an intraaortic assist balloon pump.

FIG. 1 provides a setting for the invention illustrating procedures already known in the prior art modified according to the present invention. As there shown, a catheter 2 attached to pump 4 is inserted into preferably the femoral artery 6 within body 8. According to the present invention, the catheter is attached to a balloon or balloons (not shown) which are pushed from the femoral artery up through the descending aorta, about the aortic arch 12 and into the ascending aorta 14, the lead balloon, if there is more than one, coming to rest at point y immediately adjacent the aortic valve of heart 16. A hollow wire is fed into the catheter through connection 18 and extends through the catheter and all balloons, projecting from the front end of the lead balloon in a manner to be described later. The wire 18 is connected to a pressure measuring device (not shown) since the open end of this wire within the aortic channel will be subject to the pressure therein.

More precise details of a preferred form of the invention are shown in FIGS. 2-5. As therein indicated, at the end of catheter 2 is attached a first balloon 20 positioned in the descending aorta 10. A balloon of this relative size and in this position is known in the prior art and per se forms no part of the present invention except in association with the other balloon or balloons forming part of the invention. Beyond balloon 20 and extending through the aortic arch 12 and into the ascending aorta 14 are a series of small balloons 22, 24, 26 and 28 of which the final and most effective balloon 28 is positioned adjacent the aortic valve 30. All balloons, as is known in the art, will be made of a suitable inflatable, preferably nonthrombogenic material to avoid the danger of blood clotting; polyurethane is an example of such material. The balloons are interconnected with one another by small tubes 31 (FIG. 5) which, at least for interconnecting those balloons positioned in the aortic arch, may be formed with a slight arc to facilitate insertion and placement of the multiballoon structure. The ends of the balloons are appropriately bound or otherwise sealed to the outer surface of the tubes as indicated at 32. All of the balloons are designed to permit a limited radial expansion upon inflation so that in their inflated condition they do not block the aorta. It is known that the aorta is distensible and if the patient is in shock with low blood pressure, the diameter of the aorta may contract so that if the diameter of the inflated balloon is not limited, it may effectively block the aorta. This has been found not only to reduce the effectiveness of the cardiac assist but in the extreme case with full blocking, can result in a reverse pumping action. Accordingly, limiting the diameter of the intraaortic assist balloon is an important feature of my invention.

As previously indicated with reference to FIG. 1, extending from connection 18 and through the catheter and the balloons is a hollow wire 34 which protrudes from and is sealed to the outer end 36 of balloon 28. The open end of this hollow wire is sensitive to the pressure of the blood and this pressure can be measured by connection of the other end of the tube to a known type of instrument. That portion of the hollow wire in the balloons to be positioned in the aortic arch may be formed with a slight curve or arc to facilitate placement and insertion of the multiballoon structure; such an arrangement would be used with arcuate connecting tubes, as above described.

The overall procedure for providing maximum cardiac assist utilizing the multiballoon pump of FIGS. 2–5 will now be described. The series of interconnected balloons in the deflated state, with the hollow wire in place and catheter attached, will be introduced into the femoral artery 6 and slowly urged up the descending aorta 10 and into the aortic arch 12. Prior to movement of the small balloons into the aortic arch, the balloons are inflated and since balloons 28, 26, 24 and 22 are small and of limited diameter as previously discussed, they easily conform to the shape of the aortic arch and ride along its inner surface without abrading the same. Likewise, the small balloons do not catch and perhaps injure the openings to carotid arteries 38.

Tests have indicated that the significance of the balloon pump according to the present invention lies in the placement of a balloon in the ascending aorta adjacent aortic valve 30. In order to properly position the end balloon, the inflated balloon series are urged upwardly until the forward balloon 28 moves downwardly of the ascending aorta a sufficient distance to open aortic valve 30. As measured through hollow wire 34, when the tip is in the ventricle, the systolic pressure is the same as when the tip is in the aorta. However, the diastolic pressure, measured when the tip is in the ventricle, drops to zero instead of the normally observed diastolic pressure in the aorta. The balloon is then slowly withdrawn, perhaps one-half inch, until aortic valve 30 closes, as indicated when the measured blood pressure shows a normal aortic pressure curve. This is the point of optimum positioning of the forward balloon 28. Counterpulsation by pump 4 may then be started in synchronism with the normal heart beat in a manner well known in the art.

The insertion as described above provides a maximum cardiac support. At the time of systole, blood is practically sucked from the heart which at the time of diastole coronary perfusion is increased 50–300%. This is of particular significance with reference to the adjacent coronary arteries 38. On the other hand, as previously discussed, a significant feature of the present invention lies in the discovery that a single small balloon, if properly placed, may provide a significant improvement in cardiac assist even without the use of the formerly used large balloon in the descending aorta and/or the intermediate small balloons shown in FIG. 2. A significant improvement will be obtained with a single small balloon 28 alone, as shown in FIG. 6, supplemented in some cases with just the large balloon 20 connected to balloon 28 by a short catheter section 2' (FIG. 7).

Figures 6, 7:
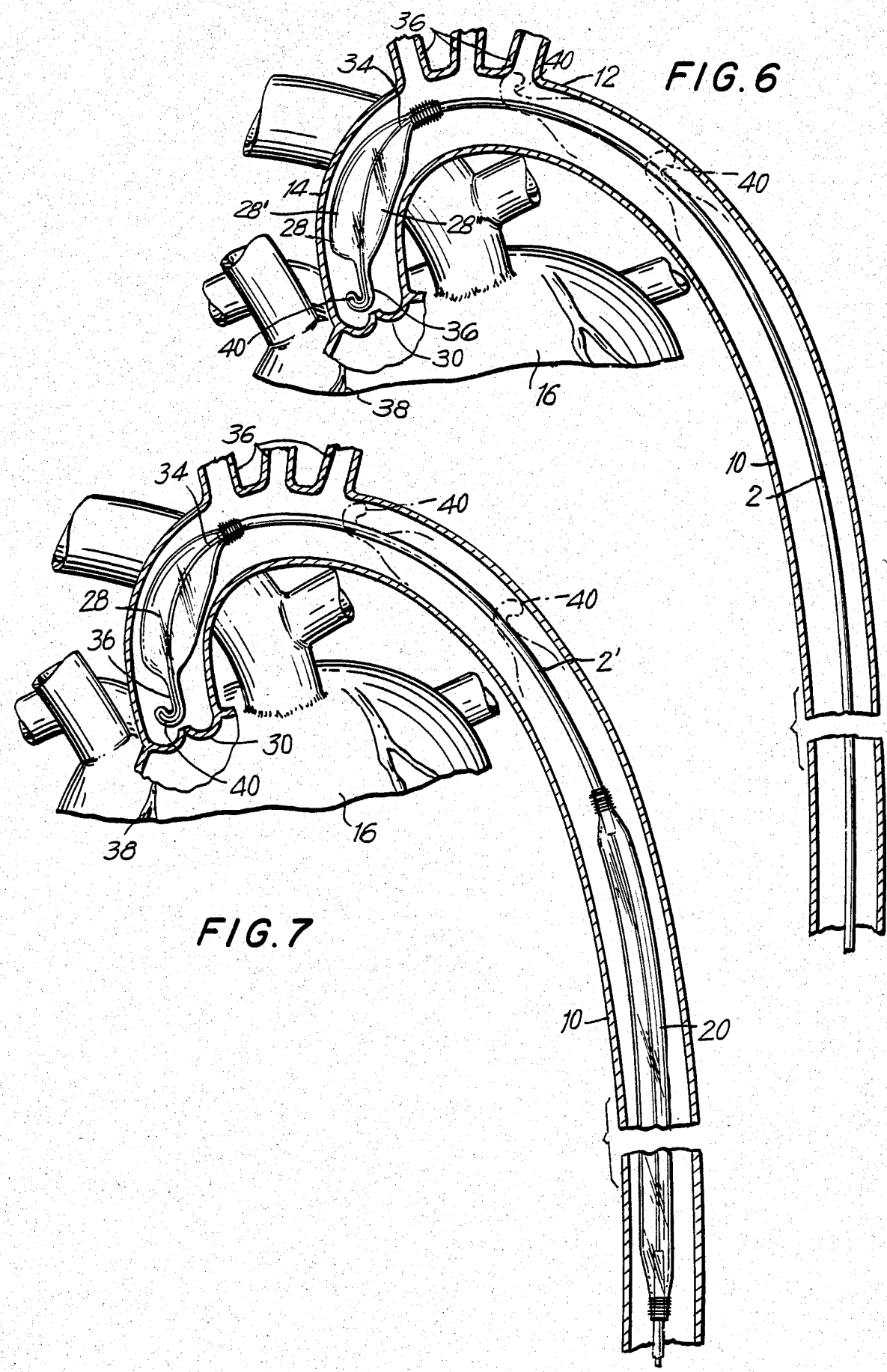
FIG. 6 is a view similar in part to FIG. 2 shown in cross-section of a modified form of balloon pump.
FIG. 7 is a view similar to FIG. 6, showing a still further modified form of balloon pump.

Attention is directed to the fact that, as shown in FIGS. 2, 6 and 7, balloons 28 and 28' positioned in the ascending aorta may be of substantially greater diameter than the balloons positioned in either the aortic arch at the descending aorta. This arrangement, which adds to the effectiveness of balloons 28 and 28', is made possible by the fact that the ascending aorta, as shown, is generally of greater diameter than the descending aorta. Thus the use of larger balloons in the critical position next to the aortic valve and the coronary arteries is made possible by taking advantage of the natural difference in size.

FIG. 6 also illustrates variations in the present invention involving significantly useful features. As previously indicated, movement of balloon 28 should proceed about aortic arch 12 in such a manner as to avoid damage to both the inner wall of the arch and the openings to carotid arteries 36. To assist in easing the balloon about the arch, the tip 36 may be formed with an arcuate section 40, curved in such a way that it will ride against the inner wall of the arch, as shown in dotted lines.

As an additional or alternate assist in guiding balloon 28 about the arch, it can be so mounted with respect to hollow wire 34 that an outer section 28' is larger than inner section 28", thus creating a larger soft outer cushion contacting the inner surface of the arch as it is pushed around.

Other variations in the invention, but falling within the scope thereof, will occur to those skilled in this art. The actual number and size of the balloons in this form of invention shown in FIG. 2 may be varied within the limits that such balloons must be capable of smooth movement about the inner wall of the aortic arch. The manner of interconnecting the balloons such as shown in FIG. 4 is not critical as long as there is a proper seal between adjacent balloons and provision is made for passage of the hollow tube 34.

Otherwise the invention as above described fulfills the objectives previously stated both as a novel medical procedure and novel apparatus for carrying out such procedure. Depending upon the effect desired, a one, two or multiple balloon system is available. The large balloon may be omitted whether one or a plurality of small balloons are used. Total balloon capacity can vary from 10 cc for one balloon as in FIG. 6 to 60 cc with a full balloon system as in FIG. 2 depending upon the amount of cardiac assist required.

As previously emphasized, however, placement of the forward balloon is of special significance and increases the amount of cardiac assist by a ratio far in excess of the mere sum of balloon capacity.

The invention is accordingly not to be considered as restricted to the exact embodiments shown and described, but only as may be limited by the claims which follow.

I claim:

1. A method of intraaortic assist which comprises introducing an inflatable member up through the descending aorta, thence about the aortic arch, and downwardly through the ascending aorta to a point immediately adjacent the aortic valve, said point being determined by monitoring the blood pressure within the aortic system, moving said inflatable member against the aortic valve until the latter is pressed open to cause a substantial drop in the ventricular pressure curve at the time of systole, and then withdrawing said inflatable member away from the valve and into the ascending aorta, thereby permitting closure of the aortic valve as indicated by return to a normal pressure curve, and rythmically inflating and deflating said inflatable member, after it is positioned adjacent the aortic valve, in synchronism with the normal beat of the heart.

2. The method of claim 1 wherein said monitoring of blood pressure within the aortic system is carried out continuously.

3. The method according to claim 1 which includes the further step of inflating said inflatable member after insertion thereof in the descending aorta and prior to movement about the aortic arch and into the ascending aorta.

4. In an intraaortic balloon pump of the type in which an inflatable balloon is attached to the end of a catheter for insertion into the aorta and having means for rythmically inflating and deflating said balloon through said catheter in rhythm with the normal heart beat, the improvement comprising forming said balloon of such size and the attached catheter of such length that the balloon may readily pass about the aortic arch to a position in the ascending aorta adjacent the aortic valve without damaging the arch and attached arteries, said balloon being larger on one side of said tube than on the other side, whereby said balloon assumes a partially arcuate shape to assist it in passing about the aortic arch, and said balloon pump further comprising an open pressure-measuring tube extending through said catheter and through said balloon.

5. In an intraaortic balloon pump according to claim 4 in which the external diameter of said balloon in its inflated condition is less than the inner diameter of the ascending aorta in a contracted condition.

6. In an aortic balloon pump according to claim 4, in which said tube projects through the front end of said balloon and in which said forward projection is formed with a bend adapted to contact the inner wall of the aortic arch for guiding the balloon in its passage about the inside of the aortic arch.

7. In an intraaortic balloon pump according to claim 4 the combination of a second inflatable balloon of substantially greater length than the first balloon, and in which said balloons are interconnected by a section of catheter of such length that when the first balloon is adjacent the aortic valve, the front end of the second balloon is positioned in the descending aorta.

8. In an intraaortic balloon pump according to claim 7, in which the inflated diameter of the first balloon is less than the inflated diameter of said second balloon.

9. In an intraaortic balloon pump according to claim 8, in combination with an open pressure-measuring tube extending through the entire length of said catheter and through both of said balloons, further characterized by said first balloon being larger on one side of said tube than on the other side, whereby said first balloon assumes a partially arcuate shape to assist it in passing about the aortic arch.

10. In an intraaortic balloon pump according to claim 9, in which said tube projects through the front of said first balloon, and in which said forward projection is formed with a bend adapted to contact the inner wall of the aortic arch for guiding the first balloon about the inside of the aortic arch.

11. In an intraaortic balloon pump according to claim 7 in combination with one or more additional balloons connected to and along the section of the catheter between said first and second balloons, each of said additional balloons being of substantially lesser length than said second balloon.

12. In an intraaortic balloon pump according to claim 11 in which said additional balloons in total extend through the aortic arch for substantially the entire longitudinal distance between the first and second balloons.

13. In an intraaortic balloon pump according to claims 7, 8, 9, 10 or 11 in which the external diameter of each of said balloons in their inflated condition is less than the internal diameter of that portion of the aorta, in which they are respectively positioned, in a contracted condition.

* * * * *